United States Patent [19]

Magnin et al.

[11] Patent Number: 4,849,508
[45] Date of Patent: Jul. 18, 1989

[54] PASTEURIZATION OF IMMUNOGLOBULIN SOLUTIONS

[75] Inventors: Anthony A. Magnin; Po-Shing Wah, both of Willowdale; Paul Dennis, Mississauga, all of Canada

[73] Assignee: Connaught Laboratories Limited, Willowdale, Canada

[21] Appl. No.: 124,622

[22] Filed: Nov. 24, 1987

[30] Foreign Application Priority Data

Nov. 25, 1986 [GB] United Kingdom ............... 8628104

[51] Int. Cl.$^4$ .................... C07K 3/00; C07K 15/06
[52] U.S. Cl. .................... 530/387; 530/389; 530/427; 424/85.8; 424/101; 424/95
[58] Field of Search .............. 530/387, 389, 427; 424/101, 85, 95

[56] References Cited

U.S. PATENT DOCUMENTS

| | | | |
|---|---|---|---|
| 3,896,241 | 7/1975 | Mabaspina | 530/416 |
| 3,930,039 | 12/1975 | Kuipers | 530/414 |
| 3,986,927 | 10/1976 | Melnick et al. | 530/387 |
| 4,075,197 | 2/1978 | Schuck et al. | 530/382 |
| 4,082,734 | 4/1978 | Stephan | 530/380 |
| 4,097,473 | 6/1978 | Lewis et al. | 530/382 |
| 4,265,924 | 5/1981 | Buhler et al. | 530/414 |
| 4,424,206 | 1/1984 | Ohmura et al. | 530/386 |
| 4,440,679 | 4/1984 | Fernandes et al. | |
| 4,446,134 | 5/1984 | Naito et al. | 530/383 |
| 4,623,717 | 11/1986 | Fernancks et al. | 530/383 |
| 4,721,777 | 1/1988 | Uemura et al. | 530/387 |

OTHER PUBLICATIONS

Colombo M., et al., Lancet 1985; 2:1-4.
Schimpf K. et al., New England J. of Medicine, 316, 918 (1987).
Horowitz, M. S. et al., Thrombosis and Hemostasis, 58 (1) p. 371 (1987).
Pelczar M. J. et al., Microbiology, 4th Ed., McGraw-Hill, 1977, pp. 833 to 835.
Edsall, J. T., Vox Sang. 46:338-340 (1984).
Rosenqvist, E., et al., Molecular Immunology, 24, No. 5, pp. 495-501 (1987).
Christian, C. L., J. Immunology 84, 112-121.
McClelland, DBL, Yap PL, Clinics in Haematology-13, No. 1 Feb. 1984.
Bovarnick et al., J. Bacteriology 59, 509-522, 1950.
Ng, P. K. et al., Thrombosis Research 39, 439-447 (1985).
WHO/BS/83.1396-Annex 2.
Alving, B. M. et al., Immunohematherapy ed. Nydegger, Academic Press (1981).
J.A.C.S. Vol. 68, pp. 459 to 475-(1946).
Vox Sang. 7, 414 (1962).
Anderson, C. L., J. Exp. Med. 156, 1794-1806 (1982).
Molecular Immunology, 23, 331-338 (1986).
Vox Sanguinis, 50, 208 (1986).
Biochemistry Journal 118, 703, (1970).
Rousseaux-Prevost et al., Mol. Imm., 19(11), 1465-1479, (1982).
Soltis et al., Immunol., 46, 411-, (1982).
Harris et al, Vox. Sang., 36, 129-136, (1979).

Primary Examiner—Margaret Moskowitz
Assistant Examiner—Jeff Kushan
Attorney, Agent, or Firm—Sim & McBurney

[57] ABSTRACT

Pasteurization of immunoglobulin solutions to inactivate viruses without significantly altering the IgG molecules or their physiological activities is obtained with minimal aggregation in the absence of any stabilizer by heating this solution to mildly-elevated temperatures at low ionic strength and mildly acid pH values.

16 Claims, No Drawings

PASTEURIZATION OF IMMUNOGLOBULIN SOLUTIONS

FIELD OF INVENTION

The present invention relates to the heating of immunoglobulin solutions, in order to decrease or eliminate the risk of viral transmission when these materials are used clinically and to decrease enzymic contaminants which can cause clinical side reactions, without concomitant deleterious effects on the structure or function of the immunoglobulin.

BACKGROUND TO THE INVENTION

Commercial immunoglobulin preparations contain principally immunoglobulin G (IgG) molecules and are widely used for replacement therapy in agammaglobulinemia and hypogammaglobulinemia in passive immunization against pathogenic organisms, in prevention of Rh sensitization and in treatment of autoimmune conditions such as idiopathic thrombocytopenic purpura (ITP). The principal route of administration is by intravenous or intramuscular injection. However, high doses of immunoglobulins given intravenously have been reported to transmit NonA NonB (NANB) Hepatitis and possibly other viral infections.

Immunoglobulins are normally isolated from plasma or from placental blood by the Cohn cold alcohol procedures (see U.S. Pat. No. 2,390,074), by ion-exchange chromatography or by a variety of other published methods, which depend on the physical, chemical or immunological properties of the proteins involved.

Several procedures are being used to inactivate viruses inadvertently contaminating Factor VIII concentrates, another protein preparation made from the same human plasma pools as immunoglobulin solutions. Use of "steam", "dry heat" or "chemical" treatments, such as with beta-propionolactone (BPL) and ultraviolet irradiation or cholate/trinitro butyl phosphate (TNBP) have been attempted. A Factor VIII concentrate heated at 60° C. for 72 hours in the lyophilized state (or dry heat treatment) transmitted NANB hepatitis in 11 of 13 recipients with hemophilia (see Colombo M. et al, Lancet 1985; 2:1–4). No cases of NANB hepatitis, but three cases of hepatitis B, occurred among twenty patients given a concentrate heated in the moistened state under partial steam pressure (see Schimpf K. et al, New England J. of Medicine, 316, 918 (1987)). These procedures, however, did not result in a product freed from hepatitis contamination. The use of BPL/uv irradiation, while eliminating the viral contaminant(s), may result in the chemical modification of the protein molecules and to the formation of neo-antigens which may cause clinical reactions.

Laboratory studies have shown that cholate/TNBP has been very effective in eliminating lipid enveloped viruses from coagulation products. A limited clinical study involving seven patients who had no previous exposure to blood products indicated that no transmission of hepatitis had occurred (see Horowitz, M. S. et al. Thrombosis and Hemostasis, 58 (1) p. 371 [1987]). However, the method is applicable only to the destruction of lipid-enveloped viruses. The subsequent removal of the chemicals used in this method is unfortunately difficult.

Pasteurization, that is the application of heat to solutions, is well known to be effective for the inactivation of viruses and other organisms. The application of pasteurization to milk is commonly done at 71.7° C. for 15 seconds (see Pelczar M. J. et al, Microbiology, 4th Ed., McGraw-Hill, 1977, pp. 833 to 835). This treatment has been shown to effectively inactivate *Mycobacterium tuberculosis*, the most resistant pathogen likely present. Pasteurized normal serum albumin is not known to have transmitted any case of serum hepatitis or any other viral agent over a period of more than 35 years (see Edsall, J. T., Vox Sang.46:338–340 [1984]). The pasteurization of Factor VIII concentrate, in the presence of stabilizers such as sugars and amino acids, has greatly reduced the transmission of hepatitis (see Schimpf, K. et al, above). Pasteurization of Antithrombin III, another plasma product, in the presence of 0.5M citrate has been a required procedure for a number of years and no transmission of hepatitis has been reported following its administration.

Pasteurization of immunoglobulin solutions thus would appear to be an attractive possibility for virus inactivation. However, IgG molecules are known to aggregate upon heating in solution (see Rosenqvist, E. et al, Molecular Immunology, 24, No. 5, pp. 495–501, [1987]). In fact, heating of IgG solution at 63° C. for 15 minutes is a widely used method to produce soluble IgG aggregates. Such aggregates possess properties analogous to those of antigen-antibody complexes, namely they fix complement, bind to macrophages, and induce Arthus reactions (see Christian, C. L., J. Immunology 84, 112-121). Activation of complement system by the Fc regions of aggregated IgG molecules led to many attempts to produce a form of IgG suitable for intravenous use, either by modifying the isolation procedure of IgG from plasma, or by modification or removal of the Fc region (see McClelland D. B. L., Yap P. L., Clinics in Haematology- 13, No. 1 February 1984). Hence, the general idea that immunoglobulins cannot be heated in the solution state without the formation of aggregates has been part of the immunoglobulin chemistry for many years. Fernandes, P. M. et al. (U.S. Pat. No. 4,440,679) and Hirao, Y. et al (published European Patent Application No. 0196761) claimed that immunoglobulin can be heated in solution and retain their biochemical properties, but this procedure required the presence of large quantities of sugars or sugar alcohols as a primary stabilizer (up to 50% (w/v) or higher). An additional stabilizer, which may be a neutral amino acid, a neutral inorganic salt, an organic carboxylic acid salt or a surface active agent, is claimed by Hirao et al in the above-mentioned European patent application to provide additional stability. However, the presence of large quantities of sugars as stabilizers also can stabilize viruses. Sucrose has been used in the stabilizer formulation for the preservation of rickettsiae and viruses following lyophilization (see Bovarnick et al, J. Bacteriology 59, 509–522, [1950]). Ng P. K. et al., (see Thrombosis Research 39, 439–447 [1985]) showed that the addition of sucrose offered protection against inactivation of porcine parvovirus in the pasteurization of Factor VIII solution. In addition, the removal of large quantities of sugars or sugar alcohols from the protein solution is different.

SUMMARY OF INVENTION

The present invention permits pasteurization of immunoglobulin solutions in the absence of any stabilizer, to inactivate viruses without significantly altering the IgG molecules or their physiological activities. We have shown that when immunoglobulin solutions are heated at low ionic strength and mildly-acidic pH, biological activities are retained and minimal aggregation occurs (less than 5%). This is within the criteria recommended by WHO for immunoglobulin preparations suitable for intravenous use (see WHO/BS/83.1396 - Annex 2).

GENERAL DESCRIPTION OF INVENTION

In the present invention, pasteurization of dilute aqueous solutions of IgG, generally as an aqueous solution having a concentration of less than about 5% w/v, preferably less than 2% w/v, is carried out at a mildly-elevated temperature, generally about 35° C. to about 75° C., preferably about 50° C. to about 60° C., under mildly-acidic conditions, generally about pH 3.5 to about 6.5, preferably about 4 to about 6, at a low ionic strength, generally equivalent to a water solution. The ionic strength is less than that of an aqueous 0.05 mM NaCl solution.

The immunoglobulin solution treated in accordance with the invention generally has a low concentration of protein, usually less than about 5 wt. %, preferably less than 2% w/v.

The length of time for which the protein solution must be heated to achieve inactivation of the viruses present depends on the type and concentration of the viruses present and the temperature of heating. Typically, at least about 10 hours of heating time is required.

In experiments using Sindbis, Human Immunodeficiency-1 and Vaccinia viruses as models, it was shown that heating a dilute IgG solution at pH 4 to 6 for 10 hours at 56°-60° C. was at least as effective in destroying viruses as pasteurization of a 25% normal serum albumin solution at this temperature and more effective than pasteurization of a Factor VIII solution in the presence of sugars and glycine as stabilizers. The pasteurization of immunoglobulins also results in the decrease or elimination of certain enzymic contaminants that may cause clinical reactions (see Alving, B. M. et al, Immunohemotherapy, ed. Nydegger, Academic Press [1981]). Such contaminants can cause a shortening of non-activated partial thromboplastin time and the formation of kallikreins in in vitro assays.

The present invention is not limited to the pasteurization of immunoglobulins that are prepared for clinical use by present commercial methods, such as the Cohn fractionation but rather the method of preparation of the immunoglobulins is irrelevant to the utility of our process and immunoglobulins prepared from plasma by other methods or prepared by genetic engineering techniques and isolated from fermentation broths, as well as solutions obtained from transgenic animals, equally may be subjected to this pasteurization method.

Commercial immunoglobulins are of the type that are known as multivalent, that is the product is a mixture of antibodies against a great number of epitopes. These immunoglobulins also are known as polyclonal. The method of pasteurization of the present invention also is applicable to so-called monoclonal antibodies, that are produced from hybridoma cells and which are not multivalent but are specific for one particular epitope.

The present invention, therefore, is applicable to pasteurization of a wide variety of native and modified immunoglobulin solutions, including solutions of gammaglobulin (IgG), the mixture of immunoglobulins obtained directly from blood and comprising mainly gammaglobulin and less than 5% of other classes of immunoglobulins including IgA, IgM and IgE, intravenous immunoglobulin (IVIG), hyperimmune globulins, such as Rho(D) immune globulin and hepatitis B immune globulin, a monoclonal antibody of the IgG class, preferably of the IgG1 subclass, and a human myeloma protein of the IgG class, preferably of the IgG1 subclass.

EXAMPLES

EXAMPLE 1

This Example illustrates the pasteurization of Gammaglobulin solution.

Gammaglobulin solution was prepared from Cohn Fraction II+III, based on the alcohol precipitation method of Cohn disclosed in J.A.C.S. Vol. 68, pp.459 to 475 (1946). Fraction II was obtained by the method of Kistler et al described in VOX Sanguinis 7, 414 (1962). Fraction II was dissolved and clarified by filtration. The pH was adjusted to 4.0±0.3. Ethanol and salts were removed by diafiltration with an ultrafiltration unit (Millipore Casette System of M.W.C.O 100,000). To ensure removal of salt, the solution was dialyzed further against distilled water for 60 hours at 4° C. The protein concentration was adjusted to 1% w/v with distilled water and the pH adjusted to 5.0 with 0.1N hydrochloric acid. The solution was heated at 60° C. for 10 hours.

Samples before and after pasteurization were analyzed for the concentration of various viral and bacterial antibodies. No reduction in any of the antibody concentrations was found. No deleterious effect as a result of pasteurization was noted when the samples were tested for anticomplementary activity, prekallikrein activator activity (pKA), molecular size distribution (by size exclusion chromatography) and SDS PAGE (for protein composition). The undesirable pKA activity in the product was actually eliminated as a result of pasteurization.

The results obtained are summarized in the following Table I:

TABLE I

| Assay | Control 1% IVIG | Pasteurized 1% IVIG |
|---|---|---|
| Antibody Screen: | | |
| Measles | 1:32 | 1:32 |
| Mumps | 1:23 | 1:23 |
| Polio Type I | 8.1 u/ml | 8.1 u/ml |
| Polio Type II | 9.3 u/ml | 9.3 u/ml |
| Polio Type III | 6.9 u/ml | 7.0 u/ml |
| Rubella | 1:182 | 1:256 |
| Hemophilus flu. $b_x$ | 2.4 mcg/ml | 2.5 mcg/ml |
| Tetanus | 1.6 I.U./ml | 2.4 I.U./ml |
| Chemical | | |
| Anticomplementary (mg/CH50) | 1.2 | 1.0 |
| pKA (% BoB #2) (Prekallekrein Activator) | 4.5% | 0.0% |
| Physical | | |
| Size Exclusion Chromatography | | |
| % Aggregate | <1% | <1% |
| % Dimer | 5.5% | 4.4% |
| % Monomer | 93.5%–94.5% | 94.6%–95.6% |
| $ Degradation | 0 | 0 |

EXAMPLE 2

This Example illustrates the pasteurization of intravenous immunoglobulin (IVIG).

A lyophilized Intravenous Immunoglobulin preparation, prepared by the applicants, composed of native IgG not previously modified by chemical or enzymatic means, was reconstituted with distilled water. The solution was extensively dialyzed against distilled water at 4° C. to remove glucose and salts. The protein concentration was decreased to 1% w/v with distilled water and the pH was adjusted to 5.0 with 0.1N hydrochloric acid. The conductivity of the solution was 110 microS (25° C.). Pasteurization was performed at 60° C. for 10 hours.

The following tests were performed to ensure that no damage had been done to the IgG as a result of pasteurization:

(i) Circular dichroism spectra were determined between 210 and 320 nm for immunoglobulin solutions both before and after pasteurization. These spectra were obtained with an ORD/CD-15 spectropolarimeter at 25° C. Both CD spectra were identical.

(ii) The UV spectra of the two solutions, before and after pasteurization, were also identical between 240 and 350 nm using a Cary 219 UV/Vis spectrophotometer.

No gross conformational changes, therefore, had occurred in the three dimensional structure of the proteins as a result of pasteurizing the solution at 60° C. for 10 hours at pH 5.0.

The aggregate concentration, as determined by size exclusion chromatography, increased from less than 1% to 2% after pasteurization, still well below the 5% limit recommended by the World Health Organization (WHO) for an immunoglobulin solution suitable for intravenous use. No degradation product was detected.

However, the immunoglobulin solutions both before and after pasteurization, retain their capacity to aggregate following restoration of isotonicity and neutral pH, and after immersion in a 62.5° C. water bath for 14 minutes both samples generated about 20% of aggregate. No change in anticomplementary activity and concentrations of various antibodies were detected after pasteurization. The pKA concentration was further reduced to a "non detectable" after pasteurization.

In vitro biological activities of the immunoglobulin solutions, before and after pasteurization, were evaluated by assays involving binding of immunoglobulins to the first component of complement (C1) and measurements of competitive binding to a Fc-receptor-bearing promonocyte cell line U937. The properties of the Fc receptors in the U937 cell line have been shown to be similar in affinity and polypeptide chain structure to that of normal human monocytes and macrophages, (see Anderson, C. L., J. Exp.Med. 156, 1794–1806 [1982]). C1 binding in both samples showed normal activity with 50% inhibition at 6.5 uM and 5 uM respectively. The same samples, after heat aggregation at 62.5° C. for 14 minutes under isotonic conditions, showed 50% inhibition of $C_1$ binding at 0.0013 $\mu$M and 0.0035 $\mu$M, an increase of more than 100-fold in binding to $C_1$.

The concentrations of protein required to achieve 50% inhibition in the competitive binding to U937 Fc receptors for non-pasteurized and pasteurized samples were 15 nM and 16 nM. This was in agreement with the value of 20 nM reported by Law et al (Molecular Immunology, 23, 331–338 [1986]) for immunoglobulin preparations with intact Fc function. Gamimmune (Trade Mark of Cutter Labs), a reduced and alkylated preparation of immunoglobulin, was reported to require twice as much to achieve the same effect.

Pasteurization, therefore, did not significantly increase the binding capacity of IgG for C1 and did not affect its interaction with monocytes and macrophages. While it is difficult to correlate an in vitro test with in vivo performance, these observations suggest that no significant difference in opsonic function (through interaction between Fc and normal human monocytes and macrophages) and ability to recruit the complement system following antigen binding is found to exist between the immunoglobulin preparations before and after pasteurization.

EXAMPLE 3

This Example illustrates the pasteurization of Rho(D) Immune Globulin.

Rho(D) immune globulin powder (112 g), prepared by Cohn alcohol fractionation and treated with DEAE Sephadex A50 (Pharmacia, Sweden), was dissolved in 706 ml of distilled water. The solution was clarified by filtration through a membrane filter and desalted through a Sephadex G25 column (100 cm×10 cm). The void volume containing the protein was collected and diluted to approximately 0.5% w/v concentration.

The pH was adjusted to 4.9 with 4 ml of 1.0N hydrochloric acid. The diluted solution was filled into 500 ml vials, sealed and pasteurized in a 60° C. water bath for 11 hours. No decrease in anti-D potency was detected. The aggregate concentration in samples before and after pasteurization was below 1%. No PKA activity was detected and the anticomplementary activity was not changed after pasteurization. The results obtained are summarised in the following Table II:

TABLE II

| Test | Before | After |
|---|---|---|
| Protein Concentration | 0.5% | 0.5% |
| Anti-D Conc. (mcg/ml) | 45 | 45 |
| pKA Concentration (% BoB #2) | 1% | 0.0% |
| Anticomplementary Activity (mg/CH50) | 0.15 | 0.5% |
| Size Exclusion Chromatography (Pharmacia Superose 12 HR10/30) | | |
| Aggregate Concentration | <1% | <1% |
| Monomer + Dimer | >99% | >99% |
| Degradation Products | 0 | 0 |

EXAMPLE 4

This Example illustrates the inactivation of Sindbis and Human Immunodeficiency virus-1(HIV-1) in immunoglobulin solution by pasteurization.

(a) Comparison of virus inactivation in immunoglobulin solutions (pH 4.0 and salt free) and in Factor VIII solution containing 50% sucrose, 1M glycine (pH 7.0), was made with the use of Sindbis virus. To a 1% solution of immunoglobulin (desalted and at pH 4.0) was added an inoculum of Sindbis virus. The solution was heated at 56° C. in a water bath. Samples were withdrawn for virus infectivity assay after 0.25, 0.5, 1.0, 2.0 and 3.0 hours and immediately neutralised by the addition of 4.5% sodium carbonate solution (pH 8.0).

Similarly a 1% solution of Factor VIII, containing 50% sucrose and 1.0M glycine at pH 7.0 was spiked with an identical Sindbis virus inoculum and heated to 60° C. in a water bath. Samples were withdrawn and assayed after 0.5, 1.0, 2.0, 4.0 and 8.0 hours.

Results of residual virus infectivity, expressed as $\log_{10}$ tissue culture infective dose ($TCID_{50}$), are summarized in the following Table IIIa:

TABLE IIIa

| Sample | Treatment | Period | Log$_{10}$ TCID$_{50}$Titre |
| --- | --- | --- | --- |
| Spiked IgG Soln. (isotonic) | pH 7.0/4° C. | 0 hr. | 5.1 |
| Spiked IgG Soln. (desalted) | pH 7.0/4° C. | 0 hr. | 4.5 |
| Spiked IgG Soln. (desalted) | pH 4.0/56° C. | 0.25 hr. | <0.5 |
| Spiked IgG Soln. (desalted) | pH 4.0/56° C. | 0.5 hr. | NVD |
| Spiked IgG Soln. (desalted) | pH 4.0/56° C. | 1.0 hr. | <0 |
| Spiked IgG Soln. (desalted) | pH 4.0/56° C. | 2.0 hr. | NVD |
| Spiked IgG Soln. (desalted) | pH 4.0/56° C. | 3.0 hr. | NVD |
| Spiked 25% NSA Soln. | pH 7.0/60° C. | 0.0 hr. | 5.3 |
| Spiked 25% NSA Soln. | pH 7.0/60° C. | 0.25 hr. | 1.7 |
| Spiked 25% NSA Soln. | pH 7.0/60° C. | 0.5 hr. | 0.7 |
| Spiked 25% NSA Soln. | pH 7.0/60° C. | 1.0 hr. | NVD |
| Spiked 25% NSA Soln. | pH 7.0/60° C. | 2.0 hr. | NVD |
| Spiked Factor VIII Soln. (50% Sucrose, 1M Gly) | pH 7.0/60° C. | 0 hr. | 5.1 |
| Spiked Factor VIII Soln. (50% Sucrose, 1M Gly) | pH 7.0/60° C. | 0.5 hr. | 2.9 |
| Spiked Factor VIII Soln. (50% Sucrose, 1M Gly) | pH 7.0/60° C. | 1.0 hr. | 2.3 |
| Spiked Factor VIII Soln. (50% Sucrose, 1M Gly) | pH 7.0/60° C. | 2.0 hr. | <0 |
| Spiked Factor VIII Soln. (50% Sucrose, 1M Gly) | pH 7.0/60° C. | 4.0 hr. | NVD |
| Spiked Factor VIII Soln. (50% Sucrose, 1M Gly) | pH 7.0/60° C. | 8.0 hr. | NVD |

Note: NVD = No Virus Detected

A minimum reduction of 4.5 log$_{10}$TCID$_{50}$ was obtained after only 0.25 hours of heating at 56° C. for desalted immunoglobulin solutions at pH 4.0. No virus activity was detected after 2 hours and 3 hours. A similar inactivation rate of Sinbis virus in 25% Normal Serum Albumin (NSA) solution was obtained after heating at 60° C. For the stabilised Factor VIII solution, even though the heating was done at 60° C., the reduction in log$_{10}$TCID$_{50}$ was only 2.3 after 1 hour. No detection of virus was achieved after 4 hours of heating at 60° C.

(b) A similar experiment was repeated for a suspension of Human Immunodeficiency Virus-1 (HIV-1) in 25% NSA solution. The inactivation rate of HIV in 25% NSA solution was found to be much more rapid than that of Sindbis virus (See Table IIIb below). All the 8.5 logs of TCID$_{50}$ were eliminated after 8 minutes at 60° C. Because of the slower inactivation rate of Sindbis virus in the immunoglobulin solution at 56° C. and in the 25% NSA solution at 60° C., it is reasonable to assume that HIV virus infectivity, if present in the immunoglobulin solution, will be significantly decreased after pasteurization at 60° C. for 10 hours. The results obtained are shown in the following Table IIIb:

TABLE IIIb

| Sample | Residual HIV Treatment | Period | Log$_{10}$TCID$_{50}$/ml |
| --- | --- | --- | --- |
| HIV spiked 25% NSA | 60° C. | 0 min | 8.4 |
| HIV spiked 25% NSA | 60° C. | 4 min | <0 |
| HIV spiked 25% NSA | 60° C. | 8 min | NVD |
| HIV spiked 25% NSA | 60° C. | 60 min | NVD |

Note: NVD = No Virus Detected

EXAMPLE 5

This Example illustrates the inactivation of Vaccinia virus by pasteurization.

An inoculum of Vaccinia virus was added to a 1% desalted solution of immunoglobulin. The pH of the solution was 5.4. Pasteurization was done at 60° C. for 2 hours. A positive sample control was obtained by spiking a 1% desalted immunoglobulin solution (pH 6.8) with an identical virus inoculum and incubating at 37° C. for 2 hours. Residual viral infectivity was determined by titration in fertile chicken eggs and expressed in log$_{10}$PFU (pock forming units) per ml.

The results obtained are summarised in the following Table IV:

TABLE IV

| Sample | Treatment | Time | Log$_{10}$PFU/ml |
| --- | --- | --- | --- |
| Vaccinia in 1% IgG (desalted) | pH 6.8/37° C. | 2 hrs | 5.9 |
| Vaccinia in 1% IgG (desalted) | pH 5.4/60° C. | 2 hrs | NVD |
| Vaccinia in McIlvaine buffer | pH 7.6/37° C. | 2 hrs | 6.3 |
| Vaccinia in McIlvaine buffer | pH 7.6/37° C. | 24 hrs | 6.3 |

Note: NVD = No Virus Detected.

All viral infectivity (log$_{10}$PFU 6.3) was destroyed within 2 hours at 60° C. The inactivation was not due to the presence of any possible anti-Vaccinia activity that might be present in the starting immunoglobulin solution. The viral infectivity of a similarly spiked IgG solution was unaffected by incubation at 37° C. for 2 hours. The identical Vaccinia inoculum when diluted with McIlvaine buffer was found to be stable over a period of 24 hours at 37° C. Hilfenhaus et al in Vox Sanguinis, 50. 208, [1986] reported a reduction of 6.2 log$_{10}$ID$_{50}$/ml Vaccinia virus infectivity after 10 hours of pasteurization in a Factor VIII solution containing 54% sucrose and 1.8M glycine. However, complete inactivation of all the Vaccinia virus (6.7 log$_{10}$ID$_{50}$/ml) present in the sample before heat treatment was not achieved by the end of the treatment period.

Pasteurization of desalted immunoglobulin solutions at 60° C., therefore, was more effective in Vaccinia virus inactivation than the pasteurization of stabilised Factor VIII solution containing 50% sucrose and 1.0 to 2.0 M glycine.

EXAMPLE 6

This Example illustrates pasteurization of monoclonal antibodies.

Murine monoclonal antibody to lymphocytosis promoting factor (LPF, pertussis toxin) was isolated from mouse ascites fluid. The antibody was of IgG1 subclass. Following desalting of the antibody solution (0.5 mg/ml) on a G-25 column, the void volume fractions were pooled. The pH was adjusted to 5.0 with 0.06M HCl. A positive control sample was prepared by the addition of 0.02M tris hydrochloride/0.12M sodium chloride, pH 6.8. Anti-LPF activity was determined by ELISA before and after pasteurization. The inability to inactivate pertussis toxin in Chinese Hamster ovary (CHO) cells was not impaired after pasteurization.

The results obtained are summarised in the following Table V:

TABLE V

| | Anti-LPF monoclonal Desalted | |
|---|---|---|
| Test | 0 Hrs | 10 Hrs/60° C. |
| Protein Conc. | 0.1 mg/ml | 0.1 mg/ml |
| pH | 5.0 | 5.0 |
| Anti-LPF Act. | 100% | 60% |
| Inactivation of Pertussis Toxin in CHO cells | 1:320 (titre) | 1:320 (titre) |

EXAMPLE 7

This Example illustrates the pasteurization of human myeloma $IgG_1$, $IgG_2$ and $IgG_3$.

Sera were obtained from three patients with confirmed diagnoses of multiple myeloma. The three myeloma proteins were of the $IgG_1$, $IgG_2$, and $IgG_3$ subclasses. IgG was isolated from all samples by ammonium sulphate precipitation and DEAE-cellulose chromatography as described by Stevenson, G. T., and Dorrington K. J. (see Biochemical Journal 118, 703, [1970]).

The purified IgG's (1.5 ml) were dialyzed extensively against distilled water at 4° C. The dialyzed solutions were diluted to a protein concentration of 0.26% w/v and adjusted to pH 4.8±0.2 with 0.06M hydrochloric acid. Samples were heated at 60° C. for 10 hours. No generation of aggregate was detected in the $IgG_1$ solution, while 3.3% and 2.7% respectively of aggregate concentrations were found in the $IgG_2$ and $IgG_3$ solutions after pasteurization. Positive control samples of the three proteins were obtained by adding 0.02M tris hydrochloride and 0.12M sodium chloride, pH 6.8. These solutions were heated at 60° C. for 10 hours. The isotonic $IgG_1$ solution was less susceptible than $IgG_2$ or $IgG_3$ to aggregation by heating at 60° C. In fact, less than 1% of aggregate was found.

The isotonic $IgG_2$ solution contained 24% of aggregate after heating at 60° C., while 100% of the isotonic $IgG_3$ solution had been converted to insoluble aggregates.

The results obtained are summarised in the following Table VI:

TABLE VI

| Myeloma Sample | Protein conc (%) | pH | Tonicity | % Aggregate 0 hr/60° C. | % Aggregate 10 hr/60° C. |
|---|---|---|---|---|---|
| IgG1 | 0.22 | 6.8 | Isotonic | <1% | <1% |
| IgG2 | 0.24 | 6.8 | Isotonic | <1% | 24% |
| IgG3 | 0.24 | 6.8 | Isotonic | <1% | 100% |
| IgG1 | 0.26 | 4.9 | Desalted | <1% | <1% |
| IgG2 | 0.26 | 4.8 | Desalted | <1% | 3% |
| IgG3 | 0.26 | 5.0 | Desalted | <1% | 3% |

As may be seen from Table VI, for the dilute protein concentration of IgG1, little or no aggregation was observed whether the solution was isotonic or desalted under the conditions of heating. This result may be compared with the result obtained at higher concentrations and temperatures (see Table VII below).

EXAMPLE 8

This Example illustrates the pasteurization of human myeloma IgG1.

Purified $IgG_1$ from a patient with a confirmed diagnosis of multiple myeloma was isolated as described in the previous example. Purified $IgG_1$ solution at 18.3 mg/ml protein concentration (1 ml) was desalted on a G-25 column (6 cm×1 cm). The void volume fractions containing the protein were pooled and diluted with distilled water to a protein concentration of 0.46% w/v.

The pH of the solution was adjusted to 5.0 by the addition 0.06M hydrochloric acid. A positive control sample was prepared by addition of 0.02M tris hydrochloride and 0.12M sodium chloride, pH 6.8. Samples were heated for 10 hours at 65° C., 70° C. and 75° C. The results of molecular size distribution analyses are summarised in Table VII below.

This particular desalted myeloma IgG did not generate aggregate after heating at 65° C. for 10 hours. Aggregation only occurred when the material was heated at 70° C. for 10 hours. The isotonic $IgG_1$, which did not generate aggregates when heated at 60° C. in the previous example, contained 18% of aggregates after heating at 65° C. Gelation occurred when heating was performed at 70° C. or higher.

TABLE VII

| Sample Heat T °C. | Protein Conc (%) | pH | Tonicity | % Aggregates 0 Hrs | % Aggregates 10 Hrs |
|---|---|---|---|---|---|
| IgG1 (65° C.) | 0.42 | 6.8 | Isotonic | <1% | 18% |
| IgG1 (70° C.) | 0.42 | 6.8 | Isotonic | <1% | Gel |
| IgG1 (75° C.) | 0.42 | 6.8 | Isotonic | <1% | Gel |
| IgG1 (65° C.) | 0.46 | 5.0 | Desalted | <1% | <1% |
| IgG1 (70° C.) | 0.46 | 5.0 | Desalted | <1% | 75% |
| IgG1 (75° C.) | 0.46 | 5.0 | Desalted | <1% | 100% |

EXAMPLE 9

This Example illustrates the effect of ionic strength on aggregation of immunoglobulins.

Varying amounts of sodium chloride were added to a 0.5% immunoglobulin solution that had been extensively dialyzed. The pH was adjusted to 5.0 with 2 mM hydrochloric acid. Pasteurization was done at 60° C. for 10 hours for each sample. The percentage of aggregate after pasteurization was determined by size exclusion chromatography (Pharmacia FPLC, Superose 12 column).

The results obtained are summarised in the following Table VIII:

TABLE VIII

| Sample | NaCl Added | Conductivity at 25° C. | % Aggregate increase over sample without added NaCl after pasteurization |
|---|---|---|---|
| 1 | 0.0005 mM | 40 microS | 1% |
| 2 | 0.005 mM | 39 microS | 0% |
| 3 | 0.05 mM | 44 microS | 4% |
| 4 | 0.5 mM | 73 microS | 7% |
| 5 | 5.0 mM | 480 microS | 22% |
| 6 | 50.0 mM | 3900 microS | gelled |

As may be seen from these results, addition of a mere 0.05 mM sodium chloride resulted in a significant increase of aggregate formation after pasteurization. Addition of 50 mM of sodium chloride resulted in the gelling of the solution indicating protein denaturation.

From these results, it is evident that the immunoglobulin solution should have a minimum ionic strength before pasteurization to avoid aggregation of the immunoglobulin. This can be achieved by many physicochemical methods, such as dialysis, electrodialysis, gel filtration or ion-exchange.

EXAMPLE 10

This Example illustrates the effect of pH on aggregation of immunoglobulins.

Samples of a 1% immunoglobulin solution were adjusted to pH 3.0, 3.5, 4.0, 5.0 and 7.0 by the addition of either 0.1N hydrochloric acid or 0.5N sodium hydroxide. The samples then were extensively dialyzed against water, previously adjusted to the required pH. After dialysis, each immunoglobulin solution was adjusted further to the starting pH with 0.1N hydrochloric acid. The pH of samples originally at 5.0 and 7.0 did not require readjustment. Pasteurization was done at 56° C. for 9 hours for each sample.

Results of aggregate formation for the samples are summarised in the following Table IXa:

TABLE IXa

| Sample | pH | % Aggregate after 9 hrs @ 56° C. |
|---|---|---|
| 1. 1% IgG Solution | 3.0 | 43% |
| 2. 1% IgG Solution | 3.5 | 15% |
| 3. 1% IgG Solution | 4.0 | 5% |
| 4. 1% IgG Solution | 5.0 | <1% |
| 5. 1% IgG Solution | 7.0 | 13% |

As may be seen from the results of Table IXa, only samples at pH 4.0 and 5.0 produced minimal aggregate concentrations (<5%).

A similar experiment was done on 1% IgG solutions at pH's of 4.0, 4.5, 5.0, 5.5 and 6.8. The solutions were heated at 60° C. for 10 hours. Acceptable aggregate concentration (<5%) were achieved with the pH between 4.0 and 5.5.

The results obtained are shown in the following Table IXb:

TABLE IXb

| Sample | pH | % Aggregate after 10 hrs. @ 60° C. |
|---|---|---|
| 1. 1% IgG Solution | 4.0 | 2% |
| 2. 1% IgG Solution | 4.5 | <1% |
| 3. 1% IgG Solution | 5.0 | <1% |
| 4. 1% IgG Solution | 5.5 | <1% |
| 5. 1% IgG Solution | 6.8 | 34% |

EXAMPLE 11:

This Example illustrates the effect of protein concentration on aggregation of immunoglobulin.

An immunoglobulin solution at pH 4.0 was extensively diafiltered against distilled water using a Millipore ultrafiltration cassette system (100,000 MWCO) for removal of salt and ethanol. A concentrated immunoglobulin solution of 10% w/v was obtained. Dilutions of this solution were made to 3% w/v, 2% w/v and 0.5% w/v with distilled water. The pH of the solutions was adjusted to pH 4.0 and the solutions were pasteurized at 56° C. for 9 hours.

The results obtained are summarised in the following Table X:

TABLE X

| Sample | Protein Conc. | % Aggregated after 9 hrs. @ 56° C. |
|---|---|---|
| Diafiltered IgG Soln. | 3.0% | 6% |
| Diafiltered IgG Soln. | 2.0% | 4% |
| Diafiltered IgG Soln. | 0.5% | 2.6% |

The aggregate concentration was the highest for the 3% w/v immunoglobulin solution. The lowest aggregate concentration obtained was for the 0.5% solution. It is evident that lower protein concentration is preferred for pasteurization with minimal aggregate formation.

EXAMPLE 12

This Example illustrates the effect of ethanol on aggregation of immunoglobulins.

An immunoglobulin solution was extensively dialyzed at pH 5.0. Protein concentration was adjusted to 0.2% w/v by the addition of distilled water. Various quantities of ethanol were added to bring the concentrations in the samples to 0.1, 0.2, 0.5, 1.0, 2.0, 5.0 and 10% v/v. The solutions were pasteurized at 60° C. for 10 hours.

The results obtained are summarised in the following Table XI:

TABLE XI

| Sample | Etnanol Concentration % v/v | % Aggregate after 10 hrs. @ 60° C. |
|---|---|---|
| 0.2% IgG Solution | 0.0 | 1.5% |
| 0.2% IgG Solution | 0.1 | 1.0% |
| 0.2% IgG Solution | 0.2 | 1.0% |
| 0.2% IgG Solution | 0.5 | 2.0% |
| 0.2% IgG Solution | 1.0 | 2.6% |
| 0.2% IgG Solution | 2.0 | 4.5% |
| 0.2% IgG Solution | 5.0 | 20.7% |
| 0.2% IgG Solution | 10.0 | 31.7% |

The data on aggregate formation presented in Table XI indicates that ethanol concentrations above 0.5% w/v cause significant aggregation of IgG molecules.

EXAMPLE 13

This Example illustrates the reduction by pasteurization of enzymic contaminants in immunoglobulin solutions contaminations.

The enzymic contaminants that might be present in immunoglobulin preparations were substantially reduced by pasteurization. The effects on prekallekrein activator (PKA) activities and non-activated Partial Thromboplastin Time (NAPTT) are summarized in the following Table XII:

TABLE XII

| Test | Sample | Heat Treatment (HT) | Before HT | After HT |
|---|---|---|---|---|
| PKA Activity (% BoB #2) | 1% ivIG | pH5/60° C./10 hrs | 4.5% | 0% |
| PKA Activity (% BoB #2) | 5% Rho(D) | pH4/37° C./48 hrs | 28% | 3% |
| NAPTT (Control Time 151 sec) | 1% Rho(D) | pH5/60° C./10 hrs | <44 sec | 103 sec |

Pasteurization eliminated PKA activity in a 1% Intravenous immunoglobulin solution. Even treatment at pH 4 at 37° C. for 48 hours substantially reduced the PKA concentration from 28% to 3%. The NAPTT of a 1% Rho(D) after pasteurization was substantially prolonged from less than 44 seconds to 103 seconds. This indicates a reduction of procoagulant activity present in the preparation.

SUMMARY OF DISCLOSURE

In summary of this disclosure, the present invention provides a novel and unexpected method for pasteurizing solutions of immunoglobulins. Such pasteurization inactivates viruses and decreases enzymic activity without causing aggregation or loss of biological activity.

Modifications are possible within the scope of this invention.

What we claim is:

1. A method of pasteurization of an aqueous solution of an immunglobulin containing less than about 5 wt. % of protein, which comprises heating said solution, in the absence of additives, stabilizers or excipients, at a temperature of about 35° C. to about 75° C. at a pH of about 3.5 to about 6.5 at an ionic strength less than that of an 0.05 mM aqueous solution of sodium chloride for a time sufficient of effect pasteurization of said solution, whereby viruses present in said aqueous solution are inactivated while retaining the biological activity of the immunoglobulin and producing less than about 5% aggregation of the immunoglobulin.

2. The method of claim 1 wherein said immunoglobulin solution has a protein concentration less than about 2 wt. %.

3. The method of claim 1 wherein said temperature is about 50° to about 60° C.

4. The method of claim 1 wherein said solution has a pH of about 4 to about 6.

5. The method of claim 1 wherein said immunoglobulin solution has an ionic strength less than that of aqueous 0.05 mM NaCl solution, has a protein concentration less than about 2 wt. % and has a pH of about 4 to 6.

6. The method of claim 5 wherein said temperature is about 50° to about 60° C.

7. The method of claim 6 wherein said solution contains less than 0.5% w/v of ethanol.

8. The method of claim 1 wherein said aqueous solution of an immunoglobulin is an aqueous solution of gammaglobulin.

9. The method of claim 1 wherein said aqueous solution of an immunoglobulin is an intravenous immunoglobulin.

10. The method of claim 1 wherein said aqueous solution of an immunoglobulin is a hyperimmune globulin.

11. The method of claim 10 wherein said hyperimmune globulin is Rho(D) immune globulin.

12. The method of claim 10 wherein said hyperimmune globulin is hepatitis B immune globulin.

13. The method of claim 1 wherein said aqueous solution of an immunoglobulin is a monoclonal antibody of the IgG class.

14. The method of claim 1 wherein said aqueous solution of an immunoglobulin is a monoclonal antibody of the IgG1 subclass.

15. The method of claim 1 wherein said aqueous solution of an immunoglobulin is a human myeloma protein of the IgG class.

16. The method of claim 1 wherein said aqueous solution of an immunoglobulin is a human myeloma protein of the IgG1 subclass.

* * * * *